United States Patent
Payne et al.

(10) Patent No.: US 9,271,690 B2
(45) Date of Patent: *Mar. 1, 2016

(54) METHOD AND SYSTEM TO ESTIMATE VISCERAL ADIPOSE TISSUE BY RESTRICTING SUBTRACTION OF SUBCUTANEOUS ADIPOSE TISSUE TO COELOM PROJECTION REGION

(75) Inventors: Randall Kenneth Payne, Madison, WI (US); Wynn Keith Wacker, Madison, WI (US)

(73) Assignee: General Electric Company, Schenectady, NY (US)

( * ) Notice: Subject to any disclaimer, the term of this patent is extended or adjusted under 35 U.S.C. 154(b) by 213 days.

This patent is subject to a terminal disclaimer.

(21) Appl. No.: 13/976,027

(22) PCT Filed: Dec. 30, 2011

(86) PCT No.: PCT/US2011/068028
§ 371 (c)(1),
(2), (4) Date: Jun. 26, 2013

(87) PCT Pub. No.: WO2012/092533
PCT Pub. Date: Jul. 5, 2012

(65) Prior Publication Data
US 2013/0287168 A1    Oct. 31, 2013

Related U.S. Application Data

(60) Provisional application No. 61/428,939, filed on Dec. 31, 2010.

(51) Int. Cl.
*A61B 6/00* (2006.01)
*A61B 6/04* (2006.01)

(52) U.S. Cl.
CPC ............... *A61B 6/482* (2013.01); *A61B 6/469* (2013.01); *A61B 6/505* (2013.01); *A61B 6/5205* (2013.01); *A61B 6/5217* (2013.01); *A61B 6/0407* (2013.01); *A61B 6/4435* (2013.01); *A61B 6/5294* (2013.01)

(58) Field of Classification Search
CPC ..... A61B 6/482; A61B 6/5205; A61B 6/5217
See application file for complete search history.

(56) References Cited

U.S. PATENT DOCUMENTS

| 4,613,754 A | 9/1986 | Vinegar et al. |
| 4,618,826 A | 10/1986 | Smith et al. |

(Continued)

FOREIGN PATENT DOCUMENTS

| EP | 1712179 B1 | 12/2010 |
| WO | 2011029153 A1 | 3/2011 |

OTHER PUBLICATIONS

International Search Report, dated May 5, 2012, for PCT/US2011/060835.

(Continued)

*Primary Examiner* — Thomas R Artman
(74) *Attorney, Agent, or Firm* — Global Patent Operation; Marc A. Vivenzio

(57) ABSTRACT

A method and system for estimating the visceral adipose tissue (VAT) mass or volume of a subject comprises performing a dual-energy X-ray scan of the subject; generating at least one image of the subject from the dual-energy X-ray scan; identifying a region of interest on the at least one image; dividing the region of interest into a plurality of sections; determining an outer transverse extent of a coelom or inner abdominal cavity of the subject; determining a subcutaneous adipose tissue (SAT) composition for each of the plurality of sections, wherein the SAT composition determination is restricted to an area directly anterior and posterior the coelom or inner abdominal cavity of the subject; and determining a VAT mass and/or volume for the region of interest based on the determined SAT composition for each of the plurality of section.

16 Claims, 8 Drawing Sheets

(56) References Cited

U.S. PATENT DOCUMENTS

| | | | |
|---|---|---|---|
| 4,646,334 | A | 2/1987 | Zerhouni |
| 4,663,772 | A | 5/1987 | Mattson et al. |
| 4,788,706 | A | 11/1988 | Jacobson |
| 4,818,943 | A | 4/1989 | Chandra |
| 5,222,021 | A | 6/1993 | Feldman et al. |
| 6,318,146 | B1 | 11/2001 | Madsen et al. |
| 6,674,834 | B1 | 1/2004 | Acharya et al. |
| 6,992,280 | B2 | 1/2006 | White et al. |
| 6,999,549 | B2 | 2/2006 | Sabol et al. |
| 7,151,253 | B2 | 12/2006 | Varchena et al. |
| 7,667,191 | B2 | 2/2010 | Serban et al. |
| 7,725,153 | B2 * | 5/2010 | Kelly et al. ............ 600/407 |
| 8,483,458 | B2 | 7/2013 | Payne et al. |
| 8,527,040 | B2 * | 9/2013 | Murakawa et al. ........ 600/547 |
| 8,634,609 | B2 | 1/2014 | Masumoto et al. |
| 2003/0086535 | A1 | 5/2003 | Teppaz et al. |
| 2005/0139758 | A1 | 6/2005 | White et al. |
| 2006/0074288 | A1 * | 4/2006 | Kelly et al. ............ 600/407 |
| 2006/0204063 | A1 | 9/2006 | Nakagawa |
| 2008/0130975 | A1 | 6/2008 | Hara |
| 2008/0167552 | A1 | 7/2008 | Bouchevreau et al. |
| 2010/0135561 | A1 | 6/2010 | Moulik |
| 2010/0180702 | A1 | 7/2010 | Koyamashita et al. |
| 2010/0234719 | A1 | 9/2010 | Kelly et al. |
| 2011/0295144 | A1 * | 12/2011 | Murakawa et al. ........ 600/547 |
| 2012/0155617 | A1 | 6/2012 | Dutta et al. |

OTHER PUBLICATIONS

International Search Report, dated May 1, 2012, for PCT/US2011/068163.

Park et. al. Are dual-energy X-ray absorptiometry regional estimates associated with visceral adipose tissue mass? International Journal of Obesity (2002) vol. 26, p. 978-983. entire document.

Lee et. al. Waist circumference, dual-energy X-ray absorptiometrically measured abdominal adiposity, and computed tomographically derived intra-abdominal fat area on detecting metabolic risk factors in obese women. Nutrition (2008) vol. 24, p. 625-631. entire document.

Genton et. al. Dual-Energy X-ray Absorptiometry and Body Composition: Differences between Devices and Comparison With Reference Methods. Nutrition (2002) vol. 18, p. 66-70. entire document.

Judex et. al. Qualification of adiposity in small rodents using micro-CT. Methods (Jun. 10, 2009) vol. 50, p. 14-19. entire document.

International Search Report, dated Apr. 24, 2012, for PCT/US2011/068028.

Quality Assurance in Radiology and Medicine (QRM GmbH), "Anthropomorphic Phantoms", pp. 1-4, Available online May 22, 2010, www.qrm/de/content/products/anthropomorphic.htm.

European Search Report and Opinion issued in connection with EP Application No. 12186419.3 dated Feb. 6, 2013.

Non-Final Rejection towards U.S. Appl. No. 13/253,379 dated Dec. 12, 2012.

Final Rejection towards U.S. Appl. No. 13/253,379 dated Mar. 25, 2013.

Non-Final Rejection towards U.S. Appl. No. 13/253,379 dated Sep. 6, 2013.

Non-Final Rejection towards U.S. Appl. No. 13/253,379 dated Mar. 13, 2014.

Final Rejection towards U.S. Appl. No. 13/253,379 dated Aug. 7, 2014.

Notice of Allowance towards U.S. Appl. No. 13/977,111 dated Apr. 8, 2015.

Non-Final Rejection towards U.S. Appl. No. 13/977,303 dated Mar. 27, 2015.

* cited by examiner

METHOD AND SYSTEM TO ESTIMATE VISCERAL ADIPOSE TISSUE BY RESTRICTING SUBTRACTION OF SUBCUTANEOUS ADIPOSE TISSUE TO COELOM PROJECTION REGION

CROSS-REFERENCE TO RELATED APPLICATIONS

This is a national stage application under 35 U.S.C. §371 (c) of prior-filed, co-pending PCT patent application serial number PCT/US2011/068028, filed on Dec. 30, 2011, which claims priority to U.S. Provisional Patent Application No. 61/428,939, filed on Dec. 31, 2010, the entire contents of which are incorporated herein by reference.

BACKGROUND OF THE INVENTION

This disclosure relates generally to imaging methods and systems, and more particularly to medical diagnostic imaging methods and systems that acquire and process tissue information for measuring the visceral adipose tissue (VAT) of a subject.

Characteristics of a subject, such as body weight, fat mass, height, girth, gender, age, etc. are clinical descriptors useful by physicians to predict certain health risks that may increase or decrease mortality and morbidity risk. For example, the amount or type of abdominal fat, such as subcutaneous adipose tissue (SAT) or subcutaneous fat and VAT or visceral fat are associated with, and useful predictors of, an adverse metabolic risk profile and certain diseases, such as coronary heart disease, diabetes and stroke. In addition, measuring visceral fat, for example, can relate to metabolic syndrome (i.e., a combination of medical problems that can increase the risk of heart disease, diabetes and/or stroke). People suffering from metabolic syndrome can have some or all of the following: high blood glucose, high blood pressure, abdominal obesity, low high-density lipoprotein (HDL) cholesterol, high low-density lipoprotein (LDL) cholesterol, high total cholesterol and/or high triglycerides.

Conventional methods and systems for measuring VAT are mostly performed using anthropomorphic gauges, bioimpedance gauges, weight scales, etc. These devices often are not capable of providing accurate measurements of VAT because the actual fat content is not being measured, certain assumptions and/or estimates are made during the calculation process, and/or the devices are not exactly calibrated. Also, reproducibility may be difficult, leading to inaccurate comparisons between examinations.

Medical diagnostic imaging systems, such as computed tomography (CT) imaging systems or magnetic resonance (MR) imaging systems have also been used to measure VAT content. However, the use of these systems is often very costly and can expose a subject to high levels of ionizing radiation, for example, when using a CT imaging system. Additionally, these imaging systems are not always available for clinical use and may have long scan times. Moreover, certain measurements are inaccurate in larger subjects.

More sophisticated methods and systems for determining VAT often use simple models to approximate the abdominal volume of a subject from an estimate of subcutaneous fat thickness measurements. However, these methods and systems often fail to accurately estimate SAT, thereby resulting in an inaccurate estimate of VAT. For example, a normal dual-energy X-ray absorptiometry (DXA) image of the abdomen is a planar two-dimensional (2D) image that cannot explicitly measure VAT because it cannot measure the thickness of SAT in the vertical plane. It has been very difficult to determine the thickness of the subcutaneous fat region around the abdomen, especially near the buttocks, since the models used in the past do not take into account differences in the thickness of the subcutaneous fat region around the abdomen near the buttocks.

Prior methods and systems for measuring or estimating VAT have subtracted an estimated SAT contribution from the total fat (SAT and VAT) of the entire abdominal region of interest of a subject. However, there are regions of SAT within the entire abdominal region of interest of a subject that are unnecessary in the estimation or calculation of VAT of the subject. The method and system of the present disclosure accurately determines the outer transverse extent of the coelom or inner abdominal cavity and subtracts an estimated SAT contribution from the total fat (SAT and VAT) of only the regions directly anterior (above) and posterior (below) the coelom. SAT beyond the coelom or inner abdominal cavity may be excluded from the estimated VAT calculation. This improves the VAT estimate by eliminating the unneeded outer boundaries of SAT. Furthermore, a new inferior posterior model eliminates reliance on an elliptical model for the SAT outer boundaries, which are known to be inaccurate due to deviations due to buttock fat and flattening of a subject from lying on a table during the method and system of the present disclosure.

Therefore, there is a need for a method and system to more accurately estimate VAT by restricting subtraction of SAT from the total fat (SAT and VAT) to only the coelom in the abdominal region of interest of a subject, and use of a non-elliptical inferior posterior model that eliminates reliance on an elliptical model for the SAT outer boundaries, which are known to be inaccurate due to differences of fat in the superior and inferior sections in the abdominal region of interest of a subject.

BRIEF DESCRIPTION OF THE INVENTION

In accordance with an aspect of the disclosure, a method and system for determining visceral adipose tissue (VAT) of a subject, the method and system comprising performing a dual-energy X-ray scan of the subject; generating at least one image of the subject from the dual-energy X-ray scan; identifying a region of interest on the at least one image; dividing the region of interest into a plurality of sections; determining an outer transverse extent of a coelom or inner abdominal cavity of the subject; determining a subcutaneous adipose tissue (SAT) composition for each of the plurality of sections, wherein the SAT composition determination is restricted to an area directly anterior and posterior the coelom or inner abdominal cavity of the subject; and determining a VAT mass or volume for the region of interest based on the determined SAT composition for each of the plurality of sections.

Various other features, aspects, and advantages will be made apparent to those skilled in the art from the accompanying drawings and detailed description thereof.

DETAILED DESCRIPTION OF THE INVENTION

Exemplary embodiments of imaging methods and systems for scanning subjects to obtain tissue information, particularly soft tissue composition information and soft tissue thickness information, for providing and displaying visceral adipose tissue (VAT) information, are described in detail below. Different methods, systems, apparatus and models are used to measure the VAT of a subject in different regions of the subject's body.

Figure 1:
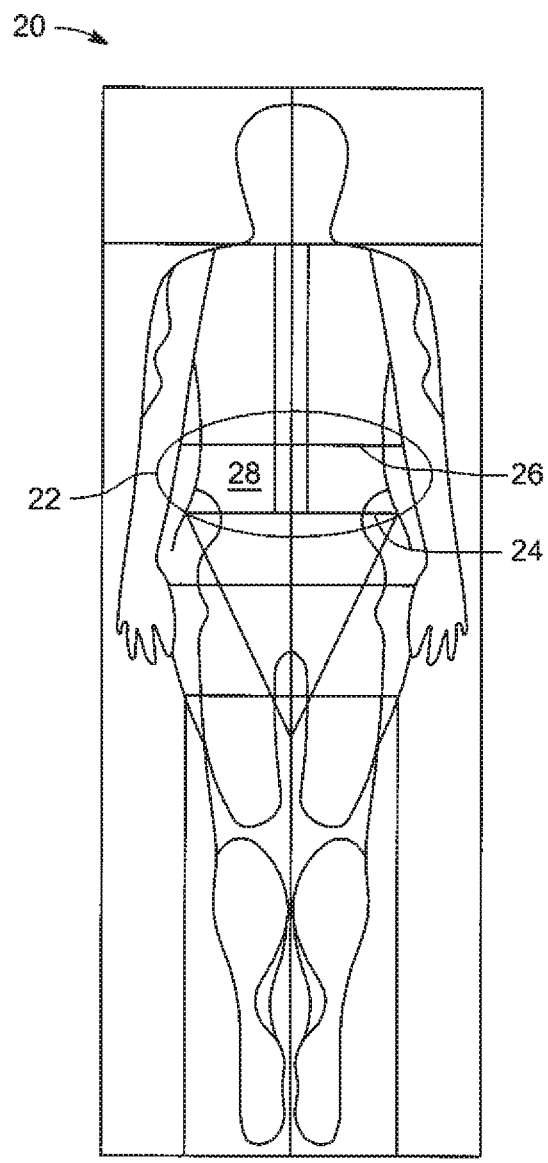
FIG. 1 is a diagram of an exemplary embodiment of a dual-energy X-ray image of a subject identifying an abdominal region of interest to determine a visceral adipose tissue (VAT) estimate of the subject.

Referring now to the drawings, FIG. 1 illustrates a diagram of an exemplary embodiment of a dual-energy X-ray image 20 of a subject identifying an abdominal region of interest 22 to determine a VAT estimate of the subject. In particular, FIG. 1 is a full body dual-energy X-ray image 20 of a subject that may be generated from a scan of the entire body of the subject using a dual-energy X-ray absorptiometry (DXA) imaging system. The illustrated dual-energy X-ray image 20 is a dual-energy soft tissue image. The image 20 is generated from a full body scan, which in some embodiments includes acquiring all bone and soft tissue information during a single scan, for example, a single imaging pass or operation. The total body scan may be acquired using different dual-energy X-ray imaging systems, for example, the Lunar iDXA imaging system available from GE Healthcare or other imaging systems. In an exemplary embodiment, the total body scan may be acquired using a computed tomography (CT) imaging system or a magnetic resonance (MR) imaging system. An embodiment of a DXA imaging system is described in more detail below in connection with FIG. 2.

The image 20 allows for the identification of different regions of interest in the imaged subject. For example, an abdominal region of interest 22 of the imaged subject can be determined using image 20. For example, based on bone and soft tissue information of the imaged subject, the abdominal region of interest 22 can be identified and the VAT thereof estimated or calculated using the acquired bone and soft tissue information. A lower boundary represented by line 24 and an upper boundary represented by line 26 of an android region 28 may be determined and identified using information acquired during the dual-energy X-ray scan, including bone and soft tissue information. The android region 28 generally corresponds to the abdominal region of interest 22 or abdomen of a subject.

In general, the image 20 formed from the DXA imaging system is a two-dimensional (2D) image of a three-dimensional (3D) subject. In particular, the image 20 is an anterior-posterior (AP) image of a subject acquired using a DXA imaging system. The image 20 may also be referred to as a posterior-anterior (PA) image of the subject. The DXA imaging system may be used to acquire both bone and soft tissue information from one or more projection measurements of X-ray attenuation at two different X-ray energy ranges. For example, when a subject is lying down on a table between an X-ray source and an X-ray detector, the X-ray detector can obtain information for an AP view of the composition of the subject, including bones and soft tissue as a result of the passage of X-rays at two different energy levels through the subject. In an exemplary embodiment, the subject may be a human patient, an animal or an object.

Figure 2:
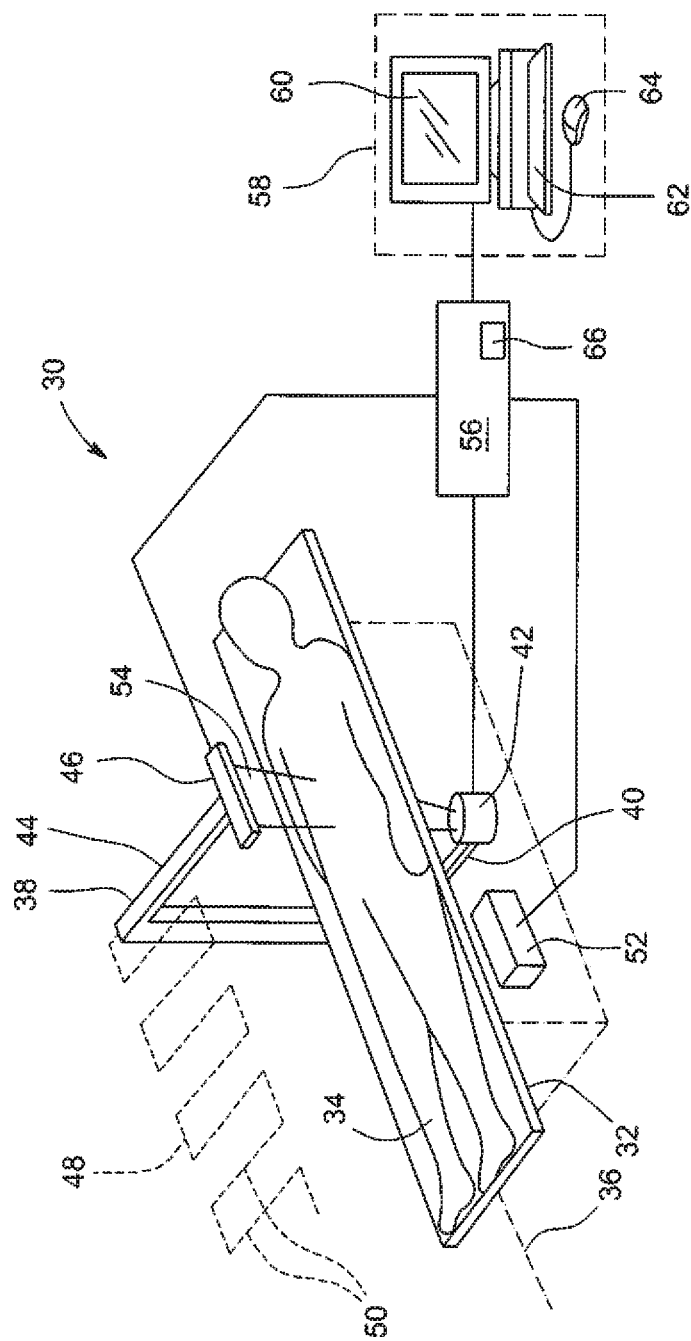
FIG. 2 is a schematic diagram of an exemplary embodiment of a dual-energy X-ray imaging system that may be used to acquire the dual-energy X-ray image of FIG. 1 and determine a VAT estimate of a subject.

FIG. 2 illustrates a schematic diagram of an exemplary embodiment of a dual-energy X-ray imaging system, illustrated as a DXA imaging system 30, which may also be referred to as dual-energy bone densitometry system capable of performing bone densitometry. The DXA imaging system 30 may be used to acquire the dual-energy X-ray image 20 of FIG. 1 and determine a VAT estimate of a subject. The system 30 is constructed in accordance with various embodiments and is configured to provide for measurement of at least soft tissue composition information, soft tissue thickness information, and bone information, including an area of a bone, a length of a bone, a bone mineral content (BMC), and a bone mineral density (BMD). The BMD is calculated by dividing the BMC by the area of the bone. During operation, two X-ray beams having different energy levels are utilized to scan a subject and provide images of the subject. The acquired images, including bone and soft tissue information from the imaged subject, particularly soft tissue composition information and soft tissue thickness information, that is used to calculate the VAT of the abdominal region of interest of the subject.

The DXA imaging system 30 includes a table 32 providing a horizontal surface for supporting a subject 34 in a supine or lateral position along a longitudinal axis 36. The DXA imaging system 30 also includes an imaging assembly 38, for example, such as an imaging arm. The imaging assembly 38 includes a lower arm portion 40 that is positioned beneath the table 32 and supports an X-ray source 42 positioned at one end thereof. The imaging assembly 38 also includes an upper arm portion 44 that is positioned above the table 32 and supports an X-ray detector 46 at one end thereof. The imaging assembly 38 is configured such that the lower arm portion 40 and the upper arm portion 44 are coupled together so that the X-ray source 42 and the X-ray detector 46 move in unison with each other. However, it should be noted that the position of the X-ray source 42 and the X-ray detector 46 may be reversed. The X-ray detector 46 may be fabricated, for example, as a multi-element cadmium-zinc-telluride (CZT) or cadmium telluride (CdTe) detector providing for energy discrimination. The X-ray source 42 and the X-ray detector 46 may be moved in a transverse raster pattern 48 so as to trace a series of transverse scans 50 of the subject 34, where the X-ray source 42 and the X-ray detector 46 move from side-to-side, perpendicular to longitudinal axis 36, along the entire length of the subject 34, during which dual-energy X-ray imaging data is collected by the X-ray detector 46. Dual-energy X-ray imaging data is collected only during transverse (side-to-side) movement of the X-ray source 42 and the X-ray detector 46. The transverse raster motion is produced by actuators (not shown) under control of a translation controller 52. During operation, the X-ray source 42 produces an X-ray fan beam 54 in a plane that is parallel to the longitudinal axis 36. However, in some embodiments, the X-ray fan beam 54 may be provided in a plane that is perpendicular to the longitudinal axis 36. The transverse raster pattern 48 is adjusted in some embodiments such that there is some overlap (e.g., slight overlap of approximately 10 percent) between successive transverse scans 50 of the X-ray fan beam 54. In an exemplary embodiment, the X-ray source 42 may also be configured to output a thin beam of X-rays, a cone beam of X-rays, or other X-ray beam configurations.

In other dual-energy X-ray imaging systems, the X-ray source and the X-ray detector may be moved in a longitudinal raster pattern so as to trace a series of longitudinal scans of the subject, where the X-ray source and the X-ray detector move from head to feet and vice versa, parallel to the longitudinal axis along the entire length of the subject.

The X-ray source 42, the X-ray detector 46, and the translation controller 52 communicate with and are under the control of a computer 56 which may include both dedicated circuitry and one or more processors having the ability to execute a stored program, for example, instructions for computer 56 that are stored in memory or firmware. In an exemplary embodiment, the computer 56 also includes a body composition module 66. The body composition module 66 may utilize the dual-energy X-ray image data, and in particular, the acquired bone and soft tissue information to estimate or calculate the VAT of a subject. During operation, the body composition module 66 in cooperation with the computer 56 directs the DXA imaging system 30 to acquire a scan of a portion of a subject or full body scan of a subject, from which bone and soft tissue information may be generated. The locations of landmarks in an image may be determined automatically, manually or semi-automatically, for example, with an operator, such as a medical or healthcare professional, adjusting automatically generated landmarks for locating and identifying regions of interest of the imaged subject. The body composition module 66 utilizes the dual-energy X-ray image data, including bone and soft tissue information to determine the VAT in one or more regions of interest of the subject. In exemplary embodiments, the body composition module 66 may be an algorithm, a software application, a software program, firmware or a combination thereof.

Referring again to FIG. 2, the computer 56 is coupled to and communicates with a workstation 58. In exemplary embodiments, the workstation 58 may include a display 60, a keyboard 62, and/or other input or output device 64, such as a mouse or a touch screen display, allowing for input and output of data, text and/or images. In some embodiments, the computer 56 is located remotely from the workstation 58. In other embodiments, the computer 56 may form a portion of the workstation 58. The computer 56 is adapted to perform one or more processing operations. The acquired bone and soft tissue information, for example, image, density and thickness information may be processed and displayed in real-time during a scanning session as the data is received. Additionally or alternatively, the bone and soft tissue information may be stored temporarily in a memory device on the computer 56 during a scanning session and then processed and displayed. The bone and soft tissue information is processed to determine the VAT in one or more regions of interest of a subject. The bone and soft tissue information may also be stored in a long-term storage device (e.g., hard drive or server) for later access, such as during a follow-up scan of the same subject, allowing monitoring of changes in the VAT of the subject. The display 60 may include one or more monitors that present subject information, including the scanned image, which may include presenting bone and soft tissue information, and estimated VAT data to an operator, such as a medical or healthcare professional, for review, diagnosis and/or analysis.

Figure 3:
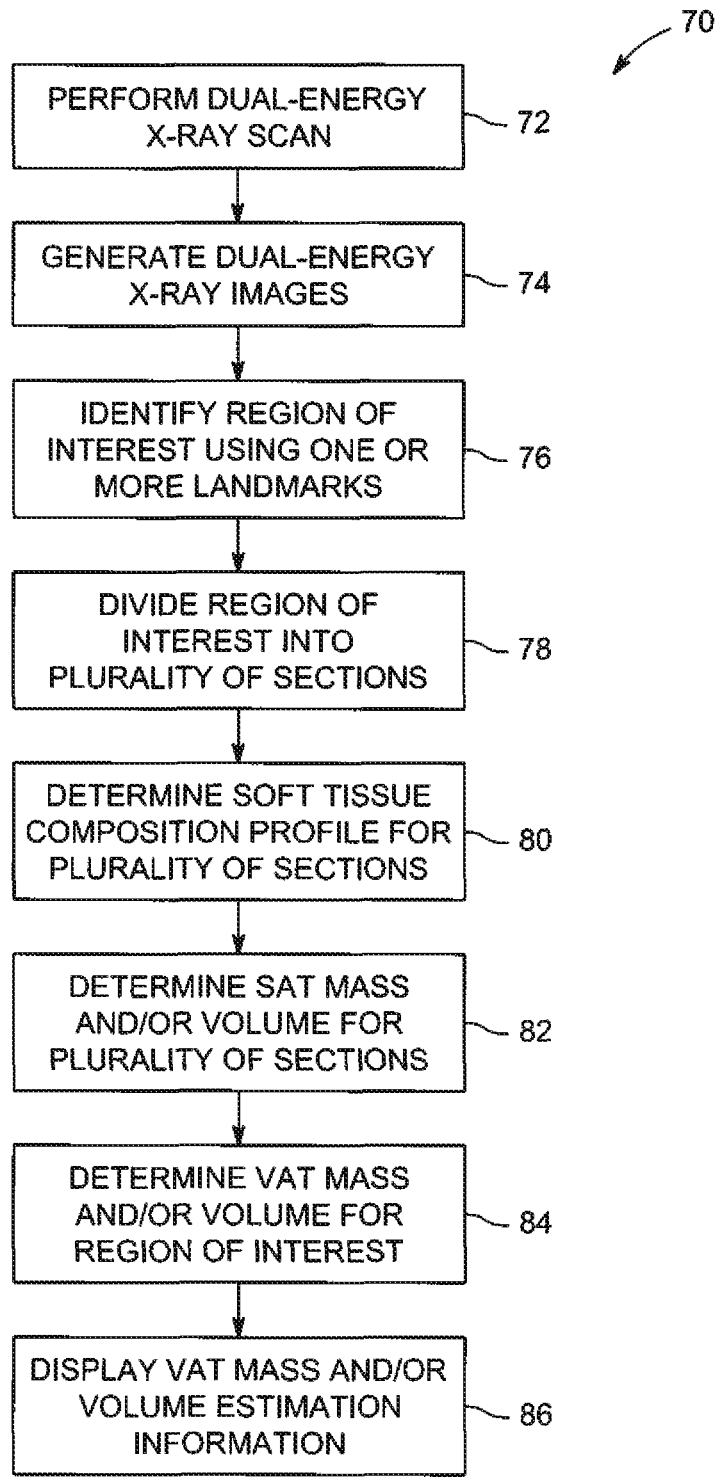
FIG. 3 is a flow diagram of an exemplary embodiment of a method for calculating VAT of a subject.

FIG. 3 illustrates a flow diagram of an exemplary embodiment of a method 70 for calculating VAT of a subject. A first step 72 in the process is performing a scan of the subject. In an exemplary embodiment, the scan may be performed by a DXA imaging system 30 performing a dual-energy X-ray scan. Using standard DXA technology, the DXA imaging system 30 generates a planar 2D soft tissue composition image and a planar 2D soft tissue thickness image. The planar 2D soft tissue composition image shows a subcutaneous adipose tissue (SAT) region of higher fat content on the sides of the abdomen. A typical soft tissue composition image shows leaner tissue being whiter and fatter tissue being darker on the image. The planar 2D soft tissue thickness image shows thicker tissue near the center of the abdomen and thinner tissue on the sides of the abdomen. A typical soft tissue thickness image shows thicker tissue being darker on the image. In an exemplary embodiment, the scan may be performed by a computed tomography (CT) scanner performing a CT scan. In an exemplary embodiment, the scan may be performed by magnetic resonance (MR) imaging system performing a MR scan.

The dual-energy X-ray scan may be a rectilinear scan of a portion of the subject or of the entire body of the subject, which may be performed in a raster-type scanning sequence. During the dual-energy X-ray scan, one or more images of a portion of or the entire subject may be acquired. These images may include bone information relating to the bones in the skeleton and soft tissue information, from which soft tissue composition and soft tissue thickness may be determined. For example, a dual-energy X-ray detector receives X-ray radiation from an X-ray beam that has passed through the subject and generates electrical signals indicating the attenuation of the X-ray radiation through the subject within distinct first and second energy ranges. Images such as bone images and tissue images, particularly soft tissue images, or a combination thereof are produced based on the attenuation of the X-ray radiation in the first and second energy ranges. The DXA imaging system 30 allows not only the formation of radiographic attenuation images, but also the mathematical analysis of the composition of the attenuating material by dual-energy X-ray imaging techniques. The dual-energy X-ray imaging techniques may be used to distinguish between bone and soft tissue, as well as to distinguish between different types of soft tissue, such as fat and lean tissue, and providing soft tissue composition information, such as fat mass, fat thickness, lean mass and lean thickness.

Figure 4:
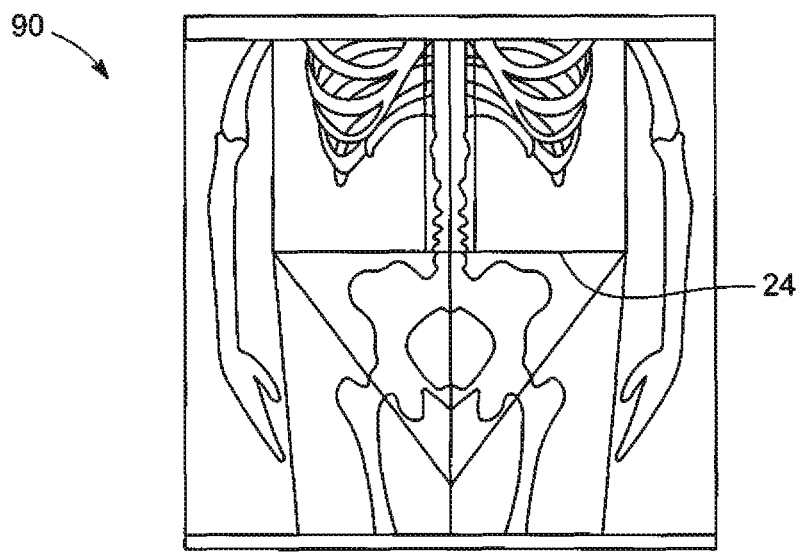
FIG. 4 is a diagram of an exemplary embodiment of a dual-energy X-ray bone image illustrating a landmark used to identify an abdominal region of interest.
Figure 5:
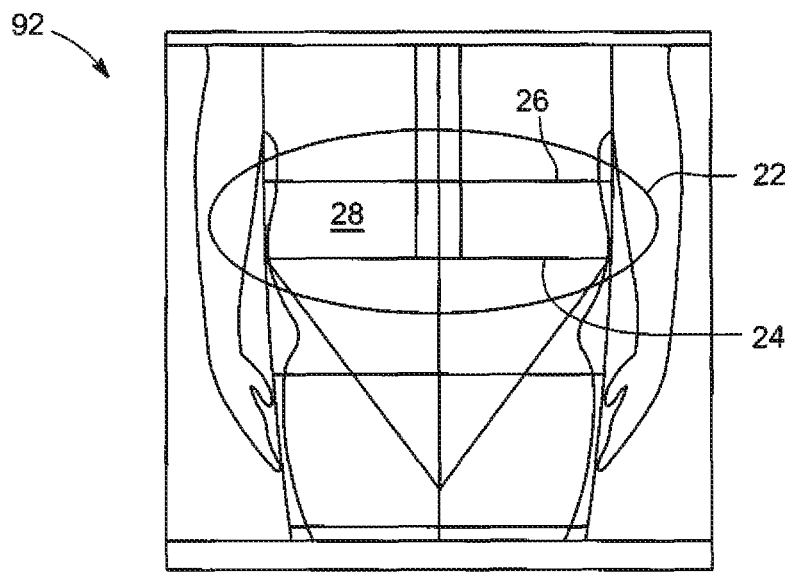
FIG. 5 is a diagram of an exemplary embodiment of a dual-energy X-ray tissue image identifying an abdominal region of interest.

After performing the dual-energy X-ray scan of a subject, one or more dual-energy X-ray images of the subject are generated in step 74, with a first image providing bone information and a second image providing soft tissue information. FIG. 4 illustrates a diagram of an exemplary embodiment of a dual-energy X-ray bone image 90 illustrating a landmark used to identify an abdominal region of interest. FIG. 5 illustrates a diagram of an exemplary embodiment of a dual-energy X-ray tissue image 92 identifying an abdominal region of interest 22.

The next step 76 in the process is identifying the region of interest using one or more landmarks in the dual-energy X-ray images. The region of interest, which in various embodiments may be the android region, abdominal region or abdomen of a subject. For example, landmarks may be identified that allow for locating one or more scan lines that encompass a region of interest, such as the android region. It should be noted that a dual-energy X-ray image may be composed of data from X-ray radiation detected by discrete pixels within the dual-energy X-ray detector. Bone and tissue information may be determined from information corresponding to attenuation of the X-ray radiation in each of the discrete pixels of the dual-energy X-ray detector. This bone and tissue information may be mapped to a gray scale to present images to an operator of the DXA imaging system.

The landmarks may correspond to different regions of interest and may be determined automatically, manually or semi-automatically. In an exemplary embodiment, landmarks may be identified to determine portions, regions or sections of images that correspond to an android region of a subject. It should be noted that the landmarks are not limited to a particular kind or type of landmark, for example, a bone, but may be an area defined by tissue or other body elements. As an example, in embodiments where an android region is to be identified, various embodiments may identify the top of the iliac crest of the pelvis, identified in dual-energy X-ray bone image 90 of FIG. 4 by the line 24, as determined from an imaged pelvis bone from a dual-energy X-ray scan as shown. The iliac crest is the thick curved upper border of the ilium, the most prominent bone in the pelvis of a human body.

The identification of the iliac crest may be performed in different ways. For example, the iliac crest may be determined manually by an operator viewing a full body dual-energy X-ray image and placing a line (e.g., using an input device) at the region of the image where the iliac crest is observed. It should be noted that the line may be defined by two endpoints or may be generated and then increased or decreased in length as needed, as well as moved or adjusted. The iliac crest also may be identified automatically using any method, for example, a template matching method or by searching for the widest bone structure in the hip region and identifying the top of that bone structure. It should be noted that when the automatic identification method is used, an operator may still adjust the identified location of the iliac crest, for example, by moving an automatically generated line. Therefore, it should be noted that any method may be used to determine the iliac crest and the identification thereof is not limited to the methods described above.

As shown in FIG. 5, the android region 28 may be determined from the top of the iliac crest defined by line 24. The android region 28 generally defines an abdominal region of interest 22 for which measurement of SAT and VAT is accordance with various embodiments is performed. For example, the android region 28 in dual-energy X-ray tissue image 92 may be defined between line 24, identifying the top of the iliac crest, and line 26, which is defined by a predetermined distance from the top of the iliac crest. In an exemplary embodiment, the distance from line 24 (i.e., the top of the iliac crest) to the top of android region 28 at line 26 may be calculated by measuring the distance from the top of the iliac crest to the bottom of the skull of the subject and multiplying that distance by 0.2. The height of the android region 28 (i.e., the distance between line 24 and 26) is defined as the android height, Ah. The distance between line 24 and line 26 is defined as twenty percent (20%) of the distance from the top of the subject's iliac crest to the bottom of the subject's skull. It should be noted that the distance between line 24 and line 26 (i.e., the android height, Ah) may also be determined from bone information from a full body scan using a pixel counting method between the two landmarks. In the pixel counting method, the distance from the top of the iliac crest to the bottom of the skull is measured using a pixel count as each pixel in the full body dual-energy X-ray image has a known size in vertical and horizontal directions. In other embodiments, line 26 may be defined by a predetermined distance from line 24, for example, ten (10) centimeters, fifteen (15) centimeters, etc. It should also be noted that the distance between line 24 and line 26 may be based in part on certain characteristics of the subject, such as the subject's height, age, etc.

Figure 6:
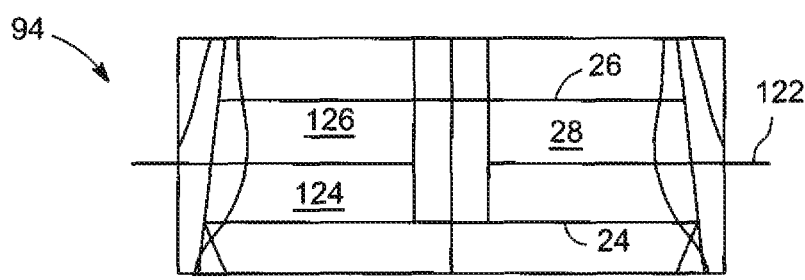
FIG. 6 is an enlarged diagram of an exemplary embodiment of a dual-energy X-ray tissue image identifying an abdominal region of interest and illustrating different sections of the abdominal region of interest.

Referring again to the method 70, once the android region 28 is identified, the next step 78 is to divide the android region 28 into a plurality of sections. The reason for dividing the android region 28 into a plurality of sections is to take into account differences in the soft tissue composition in different sections of the android region 28. FIG. 6 illustrates an enlarged diagram of an exemplary embodiment of a dual-energy X-ray tissue image 94 identifying an abdominal region of interest 28 and illustrating different sections 124, 126 of the abdominal region of interest. The android region 28 is divided in half by a line 122. The line 122 may be defined and generated by an operator or automatically defined and generated by the DXA imaging system. The android region 28 is divided by line 122 into a lower half or inferior section 124 located toward the feet of a subject undergoing a scan and an upper half or superior section 126 located toward the head of a subject undergoing a scan. The method of the present disclosure treats the inferior section 124 differently from the superior section 126. The superior section 126 is typically, but not always, above the buttocks of a subject, while the inferior section 124 usually includes the buttocks of the subject. It should be noted that the android region 28 may be divided into more than two sections. Additionally, the sections into which the android region 28 is divided may be equal in size or unequal in size.

Figure 7:
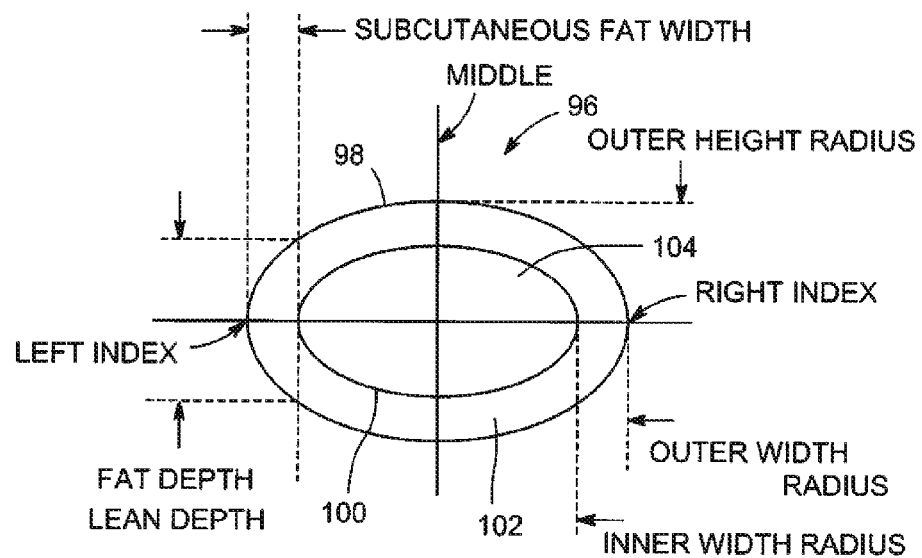
FIG. 7 is an exemplary embodiment of a diagram illustrating an elliptical model used to approximate the cross-section of an imaged section of an abdominal region of interest.

The method 70 of the present disclosure assumes an elliptical cross-section for at least the superior section 126 of the abdomen of a subject and therefore, provides an elliptical model of the superior section 126 of the android region. FIG. 7 illustrates an exemplary embodiment of a diagram illustrating an elliptical model 96 used to approximate the cross-section of an imaged section of an abdominal region of interest.

Various parameters of the elliptical model 96 of the android region 28 are shown in FIG. 7 and defined below. An outer ellipse 98 defines a region of the entire abdomen of a subject. The outer edge of the outer ellipse 98 provides an outline of the abdomen and defines the air/tissue boundary of a subject. An inner ellipse 100 defines a coelom or inner abdominal cavity 104 of a subject comprising VAT. The outer edge of the inner ellipse 100 defines the abdominal wall of a subject. The region between the outer ellipse 98 and the inner ellipse 100 defines a subcutaneous region 102 of a subject comprising SAT.

Figure 8:
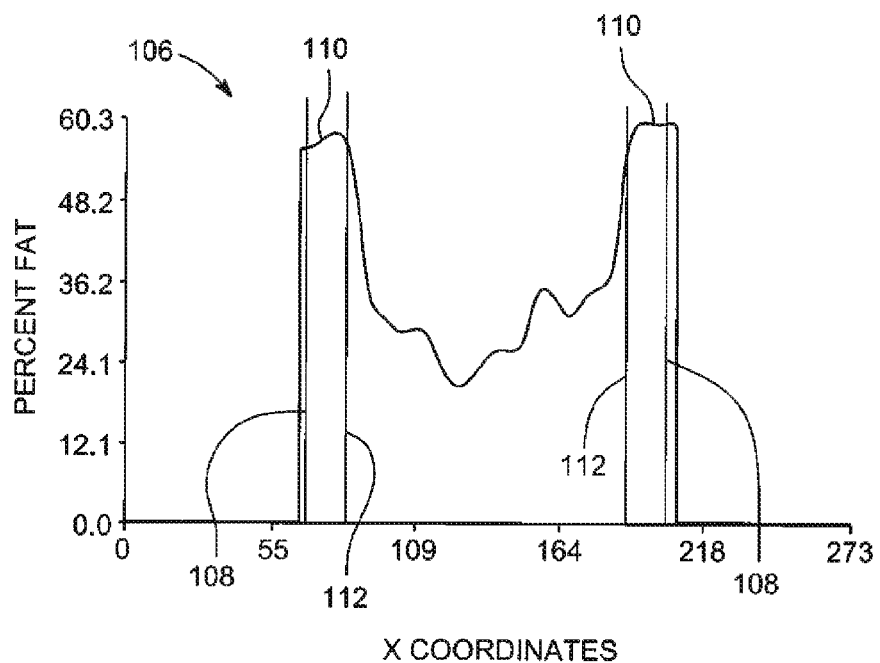
FIG. 8 is an exemplary embodiment of a soft tissue composition profile of the abdominal region of interest.

As a next step 80 in method 70, a soft tissue composition profile for each of the plurality of sections of the android region 28 is determined. In an exemplary embodiment, a separate soft tissue composition profile is determined for each superior 126 and inferior 124 section of the android region 28. The soft tissue composition profiles are based on the soft tissue composition of each of the superior and inferior section of the android region 28. An example soft tissue composition profile 106 is shown in FIG. 8. The profiles values are average body compositions over vertically integrated lines for all horizontal positions of the android region 28. This results in a soft tissue composition profile that is the composition distribution in the horizontal direction. Since DXA data contains quantum noise, the averaging of multiple lines in each section greatly reduces the noise resulting in a smooth soft tissue composition profile.

As mentioned above, FIG. 8 illustrates an exemplary embodiment of a soft tissue composition profile 106 of the abdominal region of interest. The soft tissue composition distribution has two peaks 110 at both ends of the profile 106 that represent the subcutaneous region comprising SAT.

For each left and right sides of the body of a subject, the average start of the abdomen over all vertically integrated lines in the inferior and superior section of the android region is found. A very low tissue threshold is used to find the edge of the body (i.e., air/tissue boundary) in an image, and the average transition from air to tissue is calculated. The edge of the body (i.e., air/tissue boundary) for each left and right sides of the body of a subject is identified by lines 108. The outer edge of the abdominal wall of the body of a subject is found by looking for the point of highest negative derivative, traveling towards the center of the body from the outer edge. The outer edge of the abdominal wall of the body is identified by lines 112. The search is restricted to one-fourth of the width of the abdomen, and is weighted to favor distal slopes. The average of the distance between the left pair of lines 108 and 112, and the right pair of lines 108 and 112 is used to estimate the subcutaneous region thickness. This parameter is defined as the SubcutaneousFatWidth as shown in FIG. 7. The SubcutaneousFatWidth is the distance between the outer edge of the outer ellipse 98 at the left or right index and the outer edge of the inner ellipse 100 at the left or right index. Therefore, the soft tissue composition profile is used to determine the width of the subcutaneous region (SubcutaneousFatWidth) within the android region of a subject.

Returning to FIG. 7, the height radius of the outer ellipse 98 is determined from half the peak thickness of the DXA soft tissue image. This parameter is defined as the OuterHeightRadius. The OuterHeightRadius is the distance to the outer edge of the outer ellipse 98 at the middle of the elliptical model 96 as shown in FIG. 7.

The width radius of the outer ellipse 98 is determined from half the width of the DXA soft tissue image, with lines 108 defining the outer edges of the soft tissue composition profile 106 shown in FIG. 8. This parameter is defined as the OuterWidthRadius. The OuterWidthRadius is the distance to the outer edge of the outer ellipse 98 at the left or right index from the middle of the elliptical model 96 as shown in FIG. 7.

The width radius of the inner ellipse 100 is determined from half the distance between the abdominal wall edges, with lines 112 defining the outer edge of the abdominal wall in the soft tissue composition profile 106 of FIG. 8. This parameter is defined as the InnerWidthRadius. The InnerWidthRadius is the distance to the outer edge of the inner ellipse 100 at the left or right index from the middle of the elliptical model 96 as shown in FIG. 7.

The composition of the subcutaneous region is calculated from the average of the values between the left and right subcutaneous regions 110 shown in FIG. 8. This parameter is defined as the SubcutaneousFatFraction.

Figure 11:
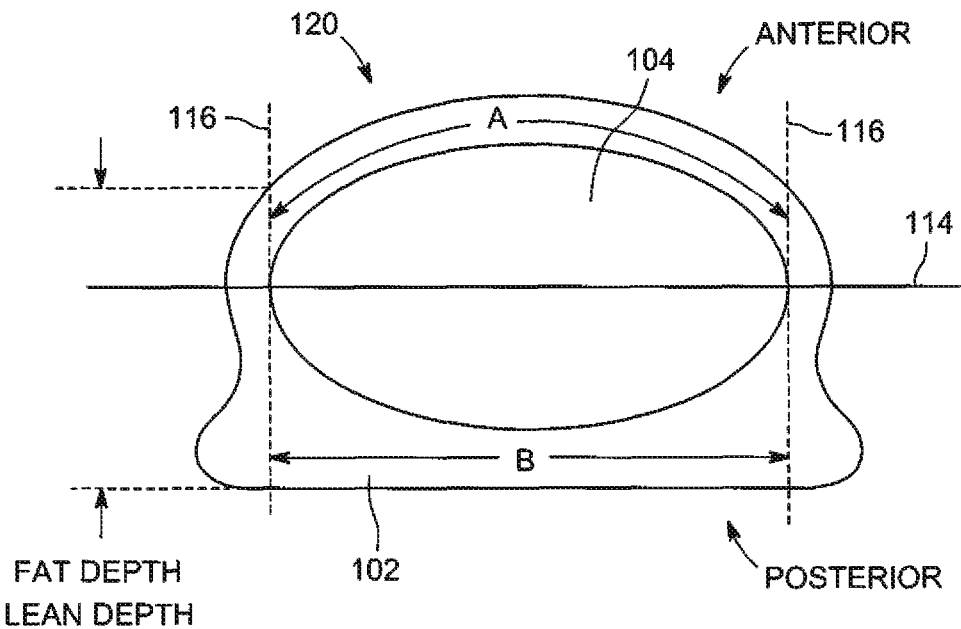
FIG. 11 is an exemplary embodiment of a diagram illustrating a non-elliptical model of the subcutaneous and visceral regions within a cross-section of an inferior section of an abdominal region of interest.

The depth of fat and lean tissue is calculated from the DXA soft tissue image at the edge of the abdominal wall. These parameters are defined as the FatDepth and LeanDepth and are shown in FIGS. 7 and 11.

To determine an estimate of the VAT of a subject, including the visceral fat and lean masses and/or volumes, the goal is to subtract off the SAT of the subject, including the subcutaneous fat and lean masses and/or volumes from the total integrated fat and lean masses and/or volumes (SAT and VAT) in the region of interest between the edges of the abdominal wall. As a next step 82 in method 70, a SAT mass and/or volume is determined for each of a plurality of sections of the android region. Since the subcutaneous fat and lean masses are different between superior and inferior sections in the region of interest of a subject, they must be calculated separately. In an exemplary embodiment, SAT masses and/or volumes are determined for superior and inferior sections.

Figure 9:
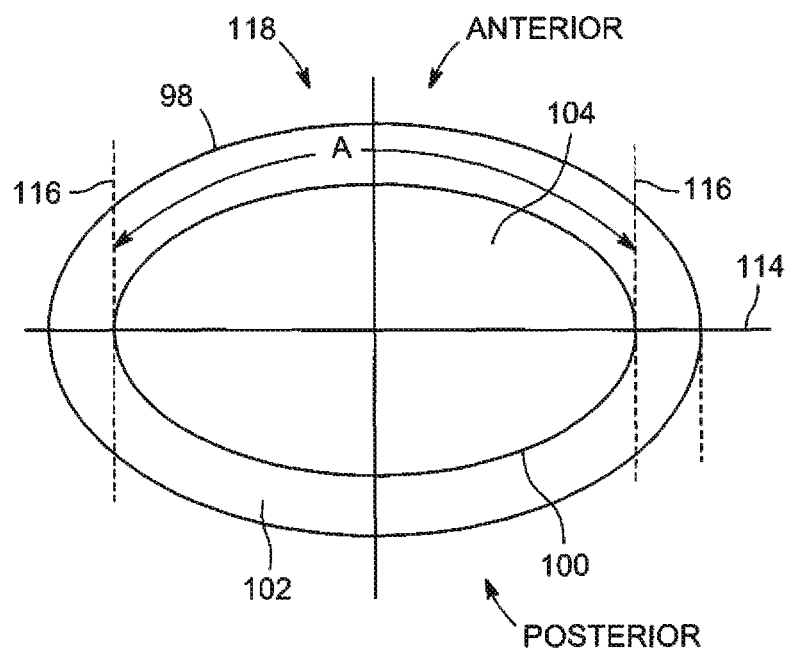
FIG. 9 is an exemplary embodiment of a diagram illustrating an elliptical model of the subcutaneous and visceral regions within a cross-section of a superior section of an abdominal region of interest.

Beginning with the superior section calculations, the method 70 of the present disclosure assumes an elliptical cross-section for the superior section of the abdomen of a subject and therefore, provides an elliptical model of the superior section of the android region. FIG. 9 illustrates an exemplary embodiment of a diagram illustrating an elliptical model 118 of the subcutaneous 102 and visceral 104 regions within a cross-section of a superior section 126 of an abdominal region of interest. The elliptical model 118 of the superior section 126 is divided in half horizontally by line 114 into an anterior portion, above line 114, representing the front side of a subject, and a posterior portion, below line 114, representing the back side of a subject. In the calculations described below, the anterior portion is treated differently than the posterior portion.

Figure 10:
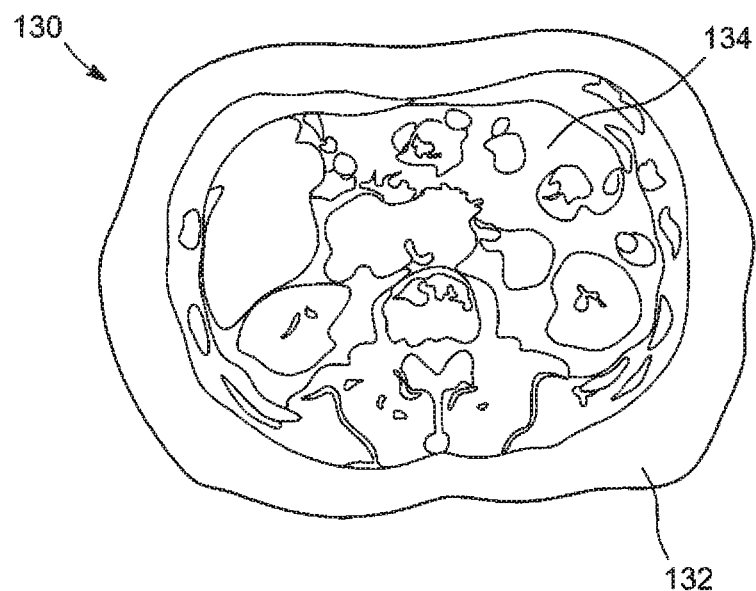
FIG. 10 is an exemplary embodiment of a cross-sectional CT image illustrating a superior section in an abdominal region of interest.

FIG. 10 illustrates an exemplary embodiment of a cross-sectional CT image 130 illustrating a superior section in an abdominal region of interest, corresponding to the elliptical model of FIG. 9. As can be seen in FIG. 10, the subcutaneous region 132 is fairly uniform all the way around the superior section in the region of interest.

In FIG. 9, the area A of the subcutaneous region in the superior anterior region is calculated by taking the area of the outer ellipse 98 between the dotted lines 116, and subtracting the area of the inner ellipse 100, and dividing by two (2).

$A=(2*\text{EllipseArea}(a,b,a-c)-\text{EllipseArea}(a,b,a)-\text{EllipseArea}(a-c,b-c,a-c))/2$; where EllipseArea($a,b,x$) is the subroutine: $(b/a)*((x*\text{sqrt}(a*a-x*x)+(a*a*a \sin(x/\text{fabs}(a)))-(a*a*a \sin(-1)))$, where $a$ is OuterWidthRadius, $b$ is OuterHeightRadius, and $c$ is SubcutaneousFatWidth ($a-c$ and $b-c$ correspond to the inner ellipse major(vertical) and minor(horizontal)axis).

For the superior anterior subcutaneous fat and lean composition calculations, the superior anterior fat and lean masses are calculated by multiplying area A by the fat and lean fraction from SubcutaneousFatFraction and by a scaling factor or constant, SuperiorAnteriorConstant, that is determined empirically to give the best correlation to CT or MR VAT estimates. These subcutaneous fat and lean masses are subtracted from the total integrated fat and lean masses within the coelom or inner abdominal cavity, that is, between dotted lines 116. In this manner, all tissue outside of the coelom, that is, outside of dotted lines 116, is ignored in the final calculation, thus eliminating any error that might occur due to inclusion of SAT in a region known to contain no coelom or VAT component.

Superior Anterior Subcutaneous Fat Mass=SuperiorAnteriorConstant*SubcutaneousFatFraction*$A$*$Ah$ Superior Anterior Subcutaneous Lean
Mass=SuperiorAnteriorConstant*(1−Subcutane-
ousFatFraction)*$A$*$Ah$ For the superior posterior subcutaneous fat and lean composition calculations, the superior posterior fat and lean masses are calculated in a similar manner as above, except with a different scaling factor or constant, SuperiorPosteriorConstant instead of SuperiorAnteriorConstant. The superior posterior fat and lean masses are calculated by multiplying area A by the fat and lean fraction from SubcutaneousFatFraction and by a scaling factor or constant, SuperiorPosteriorConstant that is determined empirically to give the best correlation to CT or MR VAT estimates. These subcutaneous fat and lean masses are subtracted from the total integrated fat and lean masses within the coelom or inner abdominal cavity, that is, between dotted lines 116. In this manner, all tissue outside of the coelom, that is, outside of dotted lines 116, is ignored in the final calculation, thus eliminating any error that might occur due to inclusion of SAT in a region known to contain no coelom or VAT component.

Figure 12:
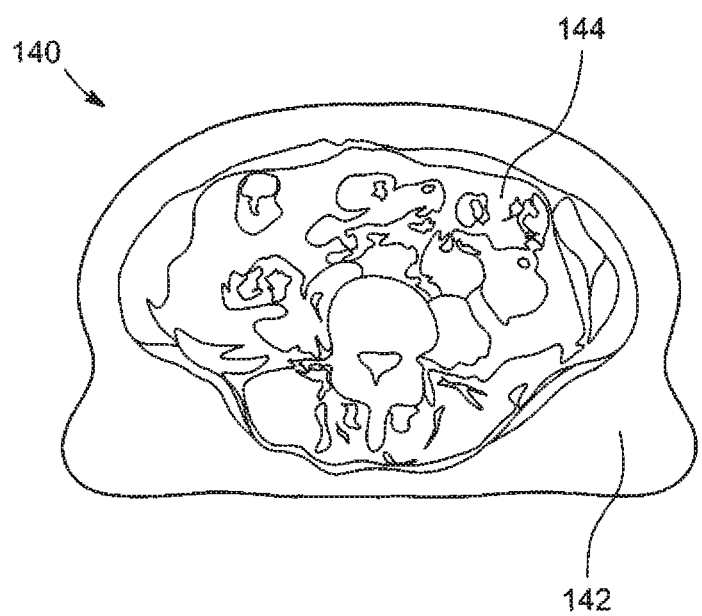
FIG. 12 is an exemplary embodiment of a cross-sectional CT image illustrating an inferior section in an abdominal region of interest.

Superior Posterior Subcutaneous Fat
Mass=SuperiorPosteriorConstant*SubcutaneousFatFraction*$A$*$Ah$ Superior Posterior Subcutaneous Lean
Mass=SuperiorPosteriorConstant*(1−SubcutaneousFatFraction)*$A$*$Ah$ Moving next to the inferior section calculations, the method 70 of the present disclosure assumes a non-elliptical cross-section for at least the inferior section of the abdomen of a subject and therefore, provides a non-elliptical model of the inferior section of the android region. FIG. 11 illustrates an exemplary embodiment of a diagram illustrating a non-elliptical model 120 of the subcutaneous 102 and visceral 104 regions within a cross-section of an inferior section 124 of an abdominal region of interest. The non-elliptical model 120 of the inferior section 124 is divided in half horizontally by line 114 into an anterior portion, above line 114, representing the front side of a subject, and a posterior portion, below line 114, representing the back side of a subject. In the calculations described below, the anterior portion is treated differently than the posterior portion. FIG. 12 illustrates an exemplary embodiment of a cross-sectional CT image 140 illustrating an inferior section in an abdominal region of interest, corresponding to the non-elliptical model of FIG. 11. As can be seen in FIGS. 11 and 12, the inferior posterior portion of the subcutaneous region 102, 142 includes the upper part of the buttocks. The inferior anterior subcutaneous region is very similar to the superior anterior subcutaneous region. The anterior portion of the subcutaneous region is very uniform from the superior section to the inferior section.

In FIG. 11, the area A of the subcutaneous region in the inferior anterior region is calculated by taking the area of the outer ellipse between the dotted lines 116, and subtracting the area of the inner ellipse, and dividing by two (2).

$A$=(2*EllipseArea($a,b,a−c$)−EllipseArea($a,b,a$)−EllipseArea($a−c,b−c,a−c$))/2; where EllipseArea($a,b,x$) is the subroutine: ($b/a$)*(($x$*sqrt($a$*$a−x$*$x$)+($a$*$a$*sin($x$/fabs($a$)))−($a$*$a$*sin(−1))), where $a$ is OuterWidthRadius, $b$ is OuterHeightRadius and $c$ is SubcutaneousFatWidth($a−c$ and $b−c$ correspond to the inner ellipse major(vertical) and minor(horizontal) axis).

For the inferior anterior subcutaneous fat and lean composition calculations, the inferior anterior fat and lean masses are calculated by multiplying area A by the fat and lean fractions from SubcutaneousFatFraction and by a scaling factor or constant, InferiorAnteriorConstant, that is determined empirically to give the best correlation to CT or MR VAT estimates. These subcutaneous fat and lean masses are subtracted from the total integrated fat and lean masses within the coelom or inner abdominal cavity, that is, between dotted lines 116. In this manner, all tissue outside of the coelom, that is, outside of dotted lines 116, is ignored in the final calculation, thus eliminating any error that might occur due to inclusion of SAT in a region known to contain no coelom or VAT component.

Inferior Anterior Subcutaneous Fat
Mass=InferiorAnteriorConstant*SubcutaneousFatFraction*$A$*$Ah$ Inferior Anterior Subcutaneous Lean
Mass=InferiorAnteriorConstant*(1−SubcutaneousFatFraction)*$A$*$Ah$ For the inferior posterior subcutaneous fat and lean composition calculations, the inferior posterior region of interest is treated differently than the other regions described above. In this case, the elliptical model is no longer used due to SAT outer boundaries, in particular, deviations in buttock SAT and flattening of SAT from a subject lying on a table undergoing the method of the present disclosure. The fat depth and lean depth at the outside edge of the abdominal wall is measured. A subcutaneous area B is estimated by multiplying the subcutaneous fat or lean depth by the inner ellipse width (coelom width), and by a scaling factor or constant, InferiorPosteriorConstant, that is determined empirically to give the best correlation to CT or MR VAT estimates.

Inferior Posterior Subcutaneous Fat
Mass=InferiorPosteriorConstant*2*InnerWidthRadius*(FatDepth−SubcutaneousFatWidth)*$Ah$ Inferior Posterior Subcutaneous Lean
Mass=InferiorPosteriorConstant*2*InnerWidthRadius*(LeanDepth−SubcutaneousFatWidth)*$Ah$ The above method step 82 calculates the mass and/or volume of the SAT strictly constrained to the region anterior (above) and posterior (below) to the coelom or inner abdominal cavity. The scaling factor or constant InferiorPosteriorConstant is used to reduce the SAT area to account for average anatomical coelom geometry in the inferior posterior region.

It should be noted that different methods and systems may be used to calculate the subcutaneous fat and lean masses of the different sections and portions, and are not limited to the methods and systems described above. For example, different profiles or models may be used for each of the different sections and portions of a particular region of interest.

As a next step 84 in method 70, a VAT mass and/or volume is determined for the region of interest. To calculate the total visceral fat and lean masses or VAT estimate of a subject, all subcutaneous fat and lean masses are subtracted from the total integrated fat and lean masses in the region of interest between the edges of the abdominal wall, within the coelom projection region.

Visceral Fat Mass=Total Integrated Fat Mass−Superior Anterior Subcutaneous Fat Mass−Superior Posterior Subcutaneous Fat Mass−Inferior Anterior Subcutaneous Fat Mass−Inferior Posterior Subcutaneous Fat Mass Visceral Lean Mass=Total Integrated Lean Mass−Superior Anterior Subcutaneous Lean Mass−Superior Posterior Subcutaneous Lean Mass−Inferior Anterior Subcutaneous Lean Mass−Inferior Posterior Subcutaneous Lean Mass The SuperiorAnteriorConstant, SuperiorPosteriorConstant, InferiorAnteriorConstant and InferiorPosteriorConstant may be adjusted to account for differences in models that achieve the best correlation to in vivo data, as measured by CT or MR scans.

Figure 13:
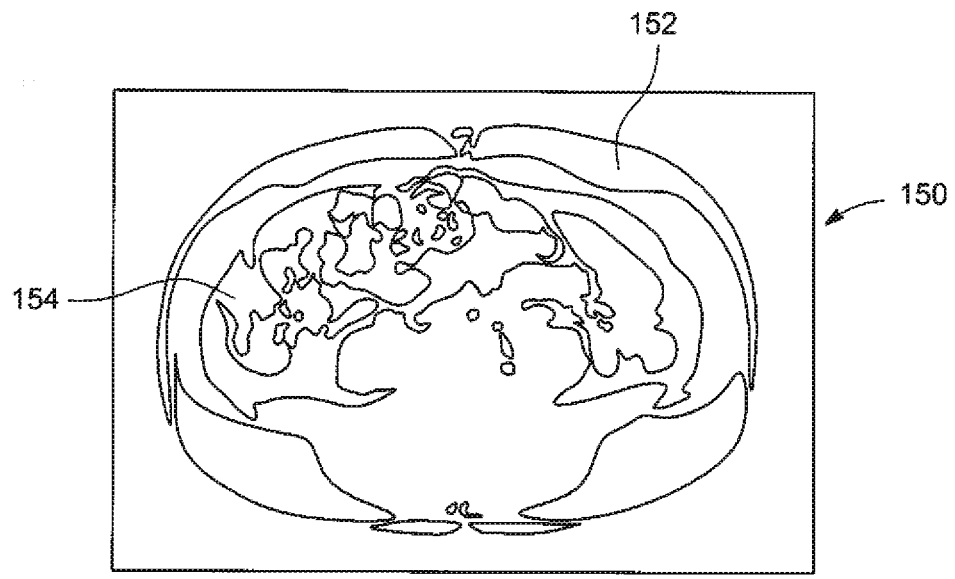
FIG. 13 is an exemplary embodiment of a cross-sectional CT image illustrating the total fat (SAT and VAT) in an abdominal region of interest of a subject.
Figure 14:
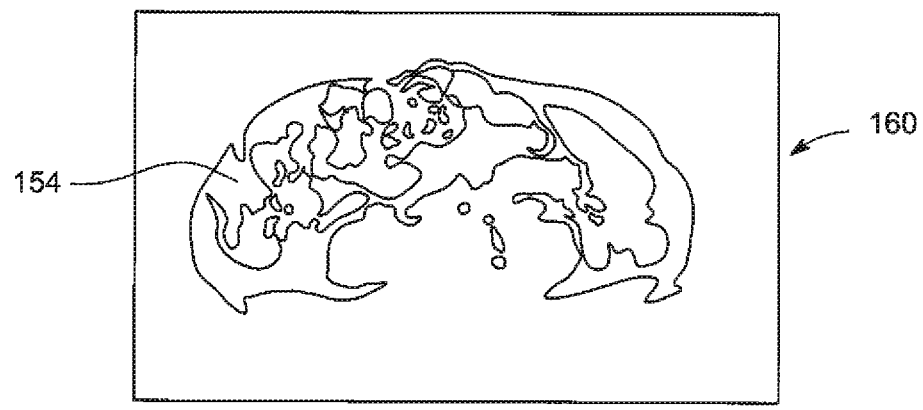
FIG. 14 is an exemplary embodiment of a cross-sectional CT image illustrating the VAT in an abdominal region of interest of a subject after removal of the subcutaneous adipose tissue (SAT) from the image.

FIG. 13 illustrates an exemplary embodiment of a cross-sectional CT image 150 illustrating the total fat (SAT 152 and VAT 154) in an abdominal region of interest of a subject. FIG. 14 illustrates an exemplary embodiment of a cross-sectional CT image 160 illustrating the VAT 154 in an abdominal region interest of a subject after removal of the SAT 152 from the image.

As a final step 86 in method 70, the VAT mass and/or volume estimation information may be displayed on the display 60 of the DXA imaging system 30, shown in FIG. 2, for review by an operator of the system.

In addition to the estimated visceral fat and lean masses, the average area density of visceral fat and lean masses over the entire android region may be calculated by taking the total visceral fat and lean masses and dividing by the height of the android region, $Ah$.

$$\text{Visceral Fat Area Density} = \text{Visceral Fat Mass}/Ah$$

$$\text{Visceral Lean Area Density} = \text{Visceral Lean Mass}/Ah$$

While the disclosure has been described with reference to various embodiments, those skilled in the art will appreciate that certain substitutions, alterations and omissions may be made to the embodiments without departing from the spirit of the disclosure. Accordingly, the foregoing description is meant to be exemplary only, and should not limit the scope of the disclosure as set forth in the following claims.

What is claimed is:

1. A method for determining visceral adipose tissue (VAT) of a subject, the method comprising:
performing a dual-energy X-ray scan of the subject;
generating at least one image of the subject from the dual-energy X-ray scan;
identifying a region of interest on the at least one image;
dividing the region of interest into a plurality of sections;
determining an outer transverse extent of a coelom or inner abdominal cavity of the subject;
determining a subcutaneous adipose tissue (SAT) composition for each of the plurality of sections, wherein the SAT composition determination is restricted to an area directly anterior and posterior the coelom or inner abdominal cavity of the subject; and
determining a VAT mass or volume for the region of interest based on the determined SAT composition for each of the plurality of sections, wherein the plurality of sections includes a first section that is modeled with an elliptical model and a second section that is modeled with a non-elliptical model.

2. The method of claim 1, wherein the dual-energy X-ray scan is a dual-energy X-ray absorptiometry (DXA) scan.

3. The method of claim 1, further comprising displaying the VAT mass or volume for the region of interest on a display of a scanning system.

4. The method of claim 1, wherein the SAT composition is subcutaneous fat mass and volume and subcutaneous lean mass and volume.

5. The method of claim 1, wherein the first section includes a subcutaneous region that is uniform.

6. The method of claim 5, wherein the first section is divided into an anterior portion on a front side of the subject and a posterior portion on a back side of the subject.

7. The method of claim 1, wherein the second section includes a subcutaneous region that is not uniform.

8. The method of claim 7, wherein the second section is divided into an anterior portion on a front side of the subject and a posterior portion on a back side of the subject.

9. The method of claim 1 wherein the models uses tissue information from at least one superior section including tissue information from an anterior and a posterior portion of the at least one superior section, and at least one inferior section including tissue information from an anterior and a posterior portion of the at least one inferior section.

10. The method of claim 1, wherein the region of interest is an android region.

11. The method of claim 1, wherein the SAT composition determination includes calculations with at least one scaling factor that is determined empirically to correlate with computed tomography (CT) or magnetic resonance (MR) VAT estimates.

12. The method of claim 11, wherein the at least one scaling factor is used to reduce SAT area to account for average coelom geometry in an inferior posterior region.

13. The method of claim 1, further comprising generating a soft tissue composition profile for each of the plurality of sections for use in determining the SAT composition for each of the plurality of sections.

14. The method of claim 13, wherein the soft tissue composition profile identifies an edge of the subject, an outer edge of an abdominal wall of the subject, and a subcutaneous thickness for each of the plurality of sections.

15. A method for determining visceral adipose tissue (VAT) of a subject, the method comprising:
performing a dual-energy X-ray scan of the subject;
generating at least one image of the subject from the dual-energy X-ray scan;
identifying a region of interest on the at least one image;
dividing the region of interest into a plurality of sections;
determining an outer transverse extent of a coelom or inner abdominal cavity of the subject;
determining a subcutaneous adipose tissue (SAT) composition for each of the plurality of sections; and
determining a VAT mass or volume for the region of interest based on the determined SAT composition for each of the plurality of sections, wherein the plurality of sections includes at least one section that is modeled with an elliptical model and at least one section that is modeled with a non-elliptical model.

16. The method of claim 15, wherein the SAT composition determination is restricted to an area directly anterior and posterior the coelom or inner abdominal cavity of the subject.

* * * * *